US007993311B2

(12) United States Patent
Finger et al.

(10) Patent No.: US 7,993,311 B2
(45) **Date of Patent: *Aug. 9, 2011**

(54) URINE COLLECTION AND DISPOSAL SYSTEM

(76) Inventors: Richard B. Finger, Houston, TX (US); James W. Meador, Houston, TX (US)

( * ) Notice: Subject to any disclaimer, the term of this patent is extended or adjusted under 35 U.S.C. 154(b) by 418 days.

This patent is subject to a terminal disclaimer.

(21) Appl. No.: 12/075,112

(22) Filed: Mar. 7, 2008

(65) Prior Publication Data

US 2008/0281282 A1 Nov. 13, 2008

(51) Int. Cl.
*A61M 1/00* (2006.01)
*A61F 5/453* (2006.01)

(52) U.S. Cl. ........................................ 604/319; 604/350

(58) Field of Classification Search .......... 604/319–323, 604/349–350
See application file for complete search history.

(56) References Cited

U.S. PATENT DOCUMENTS

| | | | | |
|---|---|---|---|---|
| 2,968,046 | A * | 1/1961 | Duke | 4/144.3 |
| 3,194,238 | A * | 7/1965 | Breece, Jr. | 604/329 |
| 3,561,445 | A | 2/1971 | Katerndahl et al. | |
| 3,626,941 | A * | 12/1971 | Webb | 604/291 |
| 3,703,731 | A * | 11/1972 | Leiser | 4/144.3 |
| 3,754,649 | A | 8/1973 | Palubniak et al. | |
| 3,863,664 | A * | 2/1975 | Holbrook et al. | 137/205 |
| 3,906,935 | A * | 9/1975 | Raia et al. | 600/575 |
| 4,270,539 | A * | 6/1981 | Frosch et al. | 604/347 |
| 4,284,079 | A * | 8/1981 | Adair | 604/349 |
| 4,345,341 | A | 8/1982 | Saito | |
| 4,345,342 | A | 8/1982 | Saito | |
| 4,360,933 | A | 11/1982 | Kimura et al. | |
| 4,366,818 | A | 1/1983 | Izumi | |
| 4,380,257 | A | 4/1983 | Howell | |
| 4,384,580 | A * | 5/1983 | Leviton | 604/320 |
| 4,385,630 | A | 5/1983 | Gilcher et al. | |
| 4,443,217 | A | 4/1984 | Izumi | |
| 4,443,219 | A * | 4/1984 | Meisch et al. | 604/317 |
| 4,490,863 | A * | 1/1985 | Pate | 4/301 |
| 4,531,939 | A | 7/1985 | Izumi | |
| 4,610,675 | A | 9/1986 | Triunfol | |
| 4,620,846 | A | 11/1986 | Goldberg et al. | |
| 4,631,061 | A | 12/1986 | Martin | |
| 4,747,166 | A | 5/1988 | Kuntz | |
| 4,784,654 | A | 11/1988 | Beecher | |

(Continued)

FOREIGN PATENT DOCUMENTS

GB 2327355 A * 1/1999

*Primary Examiner* — Jacqueline F Stephens
*Assistant Examiner* — Paula L Craig
(74) *Attorney, Agent, or Firm* — Tim L. Burgess

(57) ABSTRACT

A urine collection and disposal system and method applies subatmospheric pressure to a receptacle open to atmospheric pressure which has a urine outlet in fluid communication with a source of subatmospheric pressure. The receptacle receives urine in the receptacle from a urine donor and removes the urine from the receptacle, transporting the removed urine to a reservoir under the force of a pressure differential between atmospheric pressure at the receptacle and subatmospheric pressure at the reservoir. The reservoir urine is discharged at atmospheric pressure, for disposal, from the reservoir while maintaining the reservoir at subatmospheric pressure. A plurality of the receptacles allows simultaneously providing urine to the reservoir from more than one of the receptacles. Sanitizing fluid may be supplied intermediate the receptacle and the reservoir for transport to the reservoir under the force of the pressure differential between atmospheric and subatmospheric.

14 Claims, 3 Drawing Sheets

U.S. PATENT DOCUMENTS

| | | | | | |
|---|---|---|---|---|---|
| 4,828,546 | A | * | 5/1989 | McNeil et al. | 604/73 |
| 4,886,508 | A | * | 12/1989 | Washington | 604/327 |
| 4,921,488 | A | * | 5/1990 | Maitz et al. | 604/153 |
| 4,930,997 | A | * | 6/1990 | Bennett | 417/410.1 |
| 5,002,541 | A | * | 3/1991 | Conkling et al. | 604/319 |
| 5,195,997 | A | | 3/1993 | Carns | |
| 5,318,550 | A | * | 6/1994 | Cermak et al. | 604/349 |
| 5,336,211 | A | * | 8/1994 | Metz | 604/352 |
| 5,397,315 | A | * | 3/1995 | Schmidt et al. | 604/323 |
| 5,429,628 | A | | 7/1995 | Trinh et al. | |
| 5,551,097 | A | * | 9/1996 | Short | 4/301 |
| 5,678,564 | A | | 10/1997 | Lawrence et al. | |
| 5,741,238 | A | * | 4/1998 | Bradbury et al. | 604/322 |
| 5,792,132 | A | * | 8/1998 | Garcia | 604/385.01 |
| 5,807,359 | A | * | 9/1998 | Bemis et al. | 604/322 |
| 5,894,608 | A | | 4/1999 | Birbara | |
| 5,914,047 | A | * | 6/1999 | Griffiths | 210/739 |
| 6,007,524 | A | | 12/1999 | Schneider | |
| 6,110,159 | A | | 8/2000 | Tsujita et al. | |
| 6,311,339 | B1 | | 11/2001 | Kraus | |
| 6,394,988 | B1 | * | 5/2002 | Hashimoto | 604/355 |
| 6,493,883 | B2 | * | 12/2002 | Jones | 4/144.1 |
| 6,665,889 | B2 | * | 12/2003 | Kim | 4/443 |
| 6,945,965 | B2 | * | 9/2005 | Whiting | 604/323 |
| 7,037,303 | B2 | * | 5/2006 | Beaufore et al. | 604/537 |
| 7,351,234 | B2 | * | 4/2008 | Finger et al. | 604/319 |
| 2002/0026160 | A1 | | 2/2002 | Takahashi et al. | |
| 2002/0087131 | A1 | * | 7/2002 | Wolff et al. | 604/319 |
| 2003/0032944 | A1 | * | 2/2003 | Cawood | 604/544 |
| 2003/0171726 | A1 | | 9/2003 | Onishi et al. | |
| 2003/0195478 | A1 | | 10/2003 | Russo | |
| 2004/0176746 | A1 | | 9/2004 | Forral | |

* cited by examiner

URINE COLLECTION AND DISPOSAL SYSTEM

CROSS-REFERENCE TO RELATED APPLICATIONS

This application claims benefit of priority to U.S. Non-Provisional Patent application Ser. No. 10/962,687, filed Oct. 12, 2004, now U.S. Pat. No. 7,351,234, in turn claiming the benefit of priority to Provisional Application Ser. No. 60/510,820, filed Oct. 14, 2003.

BACKGROUND OF THE INVENTION

Collection of urine from persons who are not ambulatory and able to go to a restroom and who must or chose to urinate from a bed or bedside position, as in a hospital room, nursing home or managed care facility, and without the intervention of care giver staff, remains a problem not satisfactorily solved despite attention to the problem. The problem has been addressed both for single users and multiple users on one system. Illustrative patents are related U.S. Pat. Nos. 4,345,341; 4,360,933; 4,366,818; 4,531,939; 4,345,342; and 4,443,217, of which 4,345,342 is expressly for a multi-patient environment; see also unrelated U.S. Pat. No. 6,110,159. Particular system receptacles for male urine donors, in addition to the one described in the foregoing related patents, include those described in U.S. Pat. Nos. 5,195,997; and 6,311,339. Particular system receptacles for female urine donors include those described in U.S. Pat. Nos. 4,610,675; 4,631,061; 4,747,166; 4,784,754; 5,195,997; 5,678,564; and 6,311,339. All these systems are focused on collecting the urine, with disposal of the urine for the most part being by removal of the collector from the system for emptying or by opening a drain when the collector is full and the system is inoperative. A problem with all these systems remains how to dispose of the collected urine while maintaining the collection system in continuous operation, that is, so that a urine donor may use the system even when the system collector is full and is being emptied. The solution in U.S. Pat. No. 4,345,341 is disadvantageous in that an impeller pump must be maintained in operation in order to remove urine from the urine collector.

SUMMARY OF THE INVENTION

This invention includes method and apparatus for disposing of urine from a urine donor. The method comprises applying subatmospheric pressure to a receptacle open to atmospheric pressure and having a urine outlet in fluid communication with a source of subatmospheric pressure; receiving urine in the receptacle from a urine donor and removing the urine from the receptacle and transporting the removed urine to a reservoir in fluid communication with the source of subatmospheric pressure under the force of a pressure differential between atmospheric pressure at the receptacle and subatmospheric pressure at the reservoir; and discharging at atmospheric pressure, for disposal, urine in the reservoir while maintaining the reservoir at subatmospheric pressure. The method can include providing a plurality of the receptacles and receiving urine in the reservoir from more than one of the receptacles simultaneously, and can include supplying sanitizing fluid intermediate the receptacle and the reservoir for transport to the reservoir under the force of a pressure differential between atmospheric.

The invention includes a urine collecting and disposal system that includes a source for producing a subatmospheric pressure; a reservoir to which is applied subatmospheric pressure from the subatmospheric pressure source, a urine transport tube in valved fluid communication with the reservoir; a normally closed transport tube valve for valving fluid communication of the reservoir with the transport tube to allow or disallow subatmospheric pressure from the reservoir in the transport tube distally from the valve; a urine receptacle in fluid communication with an end of the transport tube distal from the transport tube valve and the reservoir, the receptacle having access to atmospheric air, for receiving urine from a urine donor; a switch associated with the urine receptacle for switching the transport tube valve open or closed; and a urine discharger for removal and disposal of urine from the reservoir without exposing the reservoir to atmospheric pressure, the discharger including an inlet in fluid communication with the reservoir for receiving urine at subatmospheric pressure, the inlet being sealingly closeable to maintain the inlet at subatmospheric pressure, and an outlet for discharging the urine at atmospheric pressure when the inlet is sealingly closed.

The discharge of the system may be continuous or discontinuous in operation. In a continuous discharge system, the discharger suitably comprises a peristaltic pump including a flexible tube having a proximal portion with the inlet and a distal portion with the outlet, a platen on one side of the flexible tube and at least two rollers disposed on a side of the flexible tube opposite from the platen for revolving about an axis transverse to the flexible tube, each roller having sufficient diameter that a roller pressing the proximal portion of the tubing against the platen seals the proximal portion of the tube at the subatmospheric pressure of the reservoir when another roller releases sealing on the distal portion of the flexible tubing, exposing the outlet to atmospheric pressure.

In a discontinuous discharge system, the discharger suitably includes an accumulator in normally open valved fluid communication with the reservoir for receiving urine from the reservoir and to which subatmospheric pressure is also applied from the subatmospheric pressure source, the accumulator having a normally closed discharge aperture at an inferior portion thereof for discharge of accumulated urine when the normally closed discharge aperture is opened and a normally closed superior aperture at a superior portion thereof for admission of atmospheric air when the normally closed superior aperture is opened; a normally open reservoir valve between the reservoir and the accumulator for fluid and pressure communication between the reservoir and the accumulator when open and denial of pressure communication between the reservoir and the accumulator when closed; a normally closed inferior accumulator valve operatively associated with the inferior aperture of the accumulator; a normally closed superior accumulator valve operatively associated with the superior aperture of the accumulator; an upper level switch operatively associated with the accumulator for signaling when urine is accumulated in the accumulator to a predetermined upper level; a lower level switch operatively associated with the accumulator for signaling when urine is no higher than a predetermined lower level in the accumulator; a controller operatively associated with the level switches and the reservoir and accumulator valves, for closing the normally open reservoir valve and opening the normally closed accumulator valves on receipt of a signal from the upper level switch and for closing the accumulator valves and opening the reservoir valve upon receipt of a signal from the lower level switch.

In an embodiment of the system of this invention, the receptacle has an upper opening remote from the end of the transport tube. The system further includes a disposable sheath comprising a flexible fabric insertable into the receptacle. The sheath has an inferior opening and a superior elastic opening elastically securable over a boundary of the upper opening, for sheathing the interior of the receptacle and reducing splashing of urine donated into the receptacle. In an embodiment, the sheath includes a water soluble deodorant deposited on the fabric and releasable when wetted by urine. In an embodiment, the sheath includes a water soluble sanitizing agent deposited on the fabric and releasable when wetted by urine.

In an embodiment of the system, whether continuous or discontinuous discharge, the transport tube is extendible from a normally retracted position for donation of urine into the receptacle when extended. In an embodiment, the transport tube is coilable and further comprises a tube carrier reel for retractably coiling the tube for storage in the retracted position.

In an embodiment of the system, whether continuous or discontinuous discharge, the system comprises also a sanitation wash including a source of a sanitizer; a valved conduit from the sanitizer source in fluid communication with the transport tube; and a normally closed sanitizer conduit valve for opening and closing fluid communication from the sanitizer source into the transport tube. In an embodiment of this system, the conduit is admitted into fluid communication with the transport tube downstream from the transport tube valve.

In an embodiment of the system, whether continuous or discontinuous discharge, the system comprises a plurality of urine receptacles each in valved fluid communication with a transport tube, each valved by a transport tube valve for such tube, each tube being unshared by another the receptacle, each transport tube communicating with a manifold interposed between the reservoir and the transport tube downstream from the tube valve of that transport tube.

In an embodiment of the invention including a plurality of urine receptacles and transport tubes in a urine collecting and disposal system suitable for installation in a multi-patient environment such as a hospital, nursing home or assisted care facility comprises a source for producing a subatmospheric pressure; a reservoir to which is applied subatmospheric pressure from the subatmospheric pressure source, a plurality of urine transport tubes each in valved fluid communication with the reservoir; a normally closed transport tube valve for each the transport tube for valving fluid communication of the reservoir with such transport tubes to allow or disallow subatmospheric pressure from the reservoir in such transport tube distally from the valve; a plurality of urine receptacles, each one in fluid communication with an end of one of the plurality of transport tubes, distal from the transport tube valve for such one tube, each the receptacle having access to atmospheric air, for receiving urine from a urine donor; a switch associated with each the urine receptacle for switching the transport tube valve for the one transport tube open or closed; a urine discharger for removal and disposal of urine from the reservoir without exposing the reservoir to atmospheric pressure, the discharger including an inlet in fluid communication with the reservoir for receiving urine at subatmospheric pressure, the inlet being sealingly closeable to maintain the inlet at subatmospheric pressure, and an outlet for discharging the urine at atmospheric pressure when the inlet is sealingly closed; a source of a sanitizer; a plurality of valved sanitizer conduits from the sanitizer source, each conduit being in fluid communication with a separate one of the transport tubes; and a plurality of normally closed sanitizer conduit valves, each operatively associated with a the sanitizer conduit for opening and closing fluid communication of the sanitizer source with a transport tube corresponding to a sanitizer conduit valved by the conduit valve.

In a particular embodiment of the invention, a urine collecting and disposal system suitable for installation in a multi-patient environment such as a hospital, nursing home or assisted carte facility comprises a plurality of urine receptacles each with access to atmospheric air, each for receiving urine from a urine donor; a plurality of urine transport tubes, each in valved fluid communication with one urine receptacle for receiving and transporting urine from that urine receptacle under the influence of a subatmospheric pressure applied to the urine transport tube distally from the receptacle when the tube is valved open; a normally closed transport tube valve for each transport tube distal to the urine receptacle for opening or closing the transport tube; a manifold in fluid communication with each the transport tube valved by the transport tube therefor; a source for producing a subatmospheric pressure; a reservoir to which is applied subatmospheric pressure from the subatmospheric pressure source, the reservoir being in fluid communication with the manifold for receiving urine from one or more of the transport tubes when one or more of the transport tubes is valved open to the subatmospheric pressure; a switch associated with the urine receptacle for switching the transport tube valve open or closed; an accumulator in normally open valved fluid communication with the reservoir for receiving urine from the reservoir and to which subatmospheric pressure is also applied from the subatmospheric pressure source, the accumulator having a normally closed discharge aperture at an inferior portion thereof for discharge of accumulated urine when the normally closed discharge aperture is opened and a normally closed superior aperture at a superior portion thereof for admission of atmospheric air when the normally closed superior aperture is opened; a normally open reservoir valve between the reservoir and the accumulator for fluid and pressure communication between the reservoir and the accumulator when open and denial of pressure communication between the reservoir and the accumulator when closed; a normally closed inferior accumulator valve operatively associated with the inferior aperture of the accumulator; a normally closed superior accumulator valve operatively associated with the superior aperture of the accumulator; an upper level switch operatively associated with the accumulator for signaling when urine is accumulated in the accumulator to a predetermined upper level; a lower level switch operatively associated with the accumulator for signaling when urine is no higher than a predetermined lower level in the accumulator; a source of a sanitizer; a plurality of valved sanitizer conduits from the sanitizer source, each conduit being in fluid communication with a separate one of the transport tubes; a plurality of normally closed sanitizer conduit valves, each operatively associated with a the sanitizer conduit for opening and closing fluid communication of the sanitizer source with a transport tube corresponding to a sanitizer conduit valved by the conduit valve; and a controller operatively associated with the accumulator level switches, the reservoir and accumulator valves and the sanitizer conduit valves, for closing the normally open reservoir valve and opening the normally closed accumulator valves on receipt of a signal from the upper level switch, for closing the accumulator valves and opening the reservoir valve upon receipt of a signal from the lower level switch, and for responding to a command to open one or more of the sanitizer conduit valves and open the corresponding tube valves to allow sanitizer to flow from the source through the conduit into the corresponding tube, said reservoir and said accumulator.

DETAILED DESCRIPTION OF THE INVENTION

Figure 1:
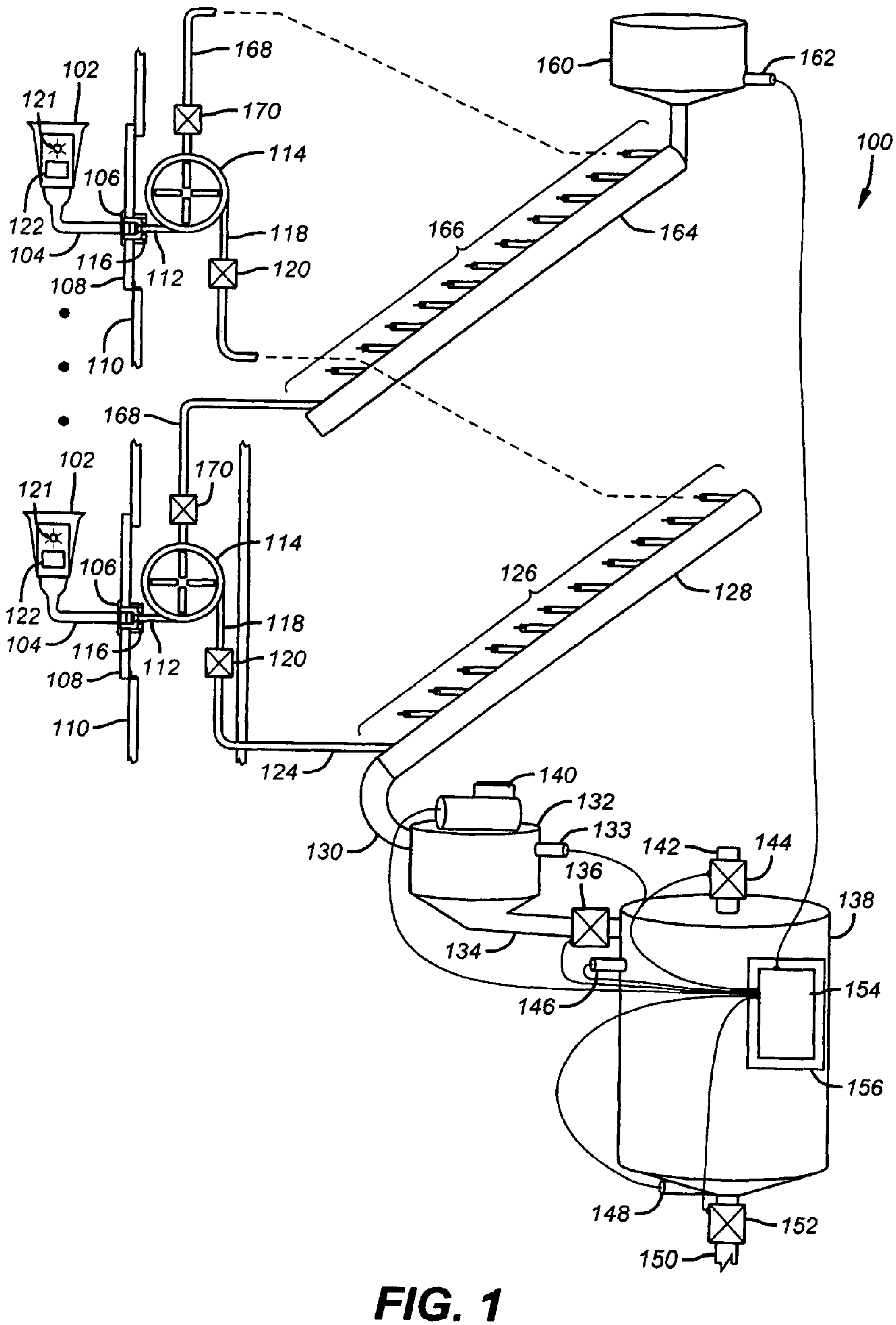
FIG. 1 is a schematic drawing showing a discontinuous discharge embodiment of the invention for use in multi-patient environments.

Referring to the drawings, FIG. 1 illustrates one embodiment of the system 100. The urine receptacle, 102 (for a male) is shown with a exit portion 104 coupled to a stopping plate 106 which resides against a hinged cover plate 108 which is mounted to a wall 110. The urine receptacle 102 is disposable and is removeably connected to a tube 112 using a barbed fitting. Tubing 112 can be pulled some distance from the wall 110 by pulling on urine receptacle and unwinding a length of tubing 112 from take-up reel 114. Tubing guide 116 permits accurate positioning of the tubing. The take up reel 114 may be spring loaded and lockable so that urine receptacle 102 may be positioned away from the wall and next to a bed as an example. The hinged cover plate 108 permits access to the take up reel 114 for removal and replacement of tubing 112. Tubing 118 is permanent tubing and has a valve such as a solenoid valve 120, which pinches the tubing or otherwise blocks the tubing from flow in its normal position. Remote switch 122 is removeably coupled to receptacle 102. When activated by the user, the remote opens the valve 120 to permit flow through the tubing 114/118. An indicator light 121 on the remote shows one color (green) when the system is operating and the receptacle is in the proper position (not inverted or lying down) or a different color (red) if it is not in the correct position or the system is not functioning. The distal portion of the tubing 124 connects to a manifold 128, which also permits other connections 126 for other people to use the system 100 in similar fashion. Manifold 128 is connected to a central line 130 and into a reservoir or receptacle 132. Receptacle 132 is connected via tubing 134 through a normally open reservoir valve 136, to accumulator or tank 138. Receptacle 132 has a vacuum pump 140 mounted to it and acts to evacuate the receptacle 132 and tank 138 of air. A float switch 133, is used as an emergency cut-off. Tank 138 also has a superior aperture or vent tube 142 with a normally closed valve 144 mounted to it. Tank 138 also has two float switches; an upper float switch 146 and a lower float switch 148. Tank 138 also has an inferior aperture or drain pipe 150 which connects to a sewer system. Drainpipe 150 has a normally closed valve 152 mounted to it. Vacuum pump 140, valves 136, 144, 152, and switches 133, 146 and 148 are in electrical connection with a computer 154 mounted inside box 156.

There can also be a sanitizing system. Receptacle 160 is a container which holds sanitizing chemicals which has a float valve 162 connected to computer 154 to signal the computer when the receptacle needs refilling. Receptacle 160 is connected to a manifold 164 which has a plurality of tubes 166 extending from manifold 164. One of these tubes 168 is shown connected to a valve 170 and in turn to tube 118.

In normal operation, vacuum pump 140 maintains a vacuum in receptacle 132, and in turn tank 138, manifold 128 and tubing 124/126. Valve 120, which is normally closed, blocks airflow to receptacle 102.

In use, a male in this case would pull on receptacle 102 from the wall with the tubing 112 unwinding from take-up reel 114 and place receptacle 102 conveniently next to him. When the urge to urinate occurs, he presses remote 122, which opens valve 120 to the vacuum source. The person then may urinate into the receptacle with the urine flowing though system 100 and into tank 138. After urinating remote switch 122 is again activated to close valve 120. Valve 120 may also be closed without pressing remote switch 122, after a fixed time delay or other means. It is the intent of this system 100 to provide sufficient vacuum and flow to allow a person to urinate without causing splashing or leaving residual urine in receptacle 102 after use. After use, or as desired, the receptacle 102 may simply be replaced with a new receptacle and the remote switch 122 being recoupled to a new receptacle 102. The user can unlock the take-up reel 114, and reposition the receptacle on the wall as shown in FIG. 1. At some point in time, either on a scheduled basis or after urinating, valve 170 opens and valve 120 opens (or remains open) to permit sanitizing chemicals to flow from the receptacle 160, through manifold 164 and to tube 118 to clean the permanent portion of the system.

Once tank 138 fills and activates the float switch 146, then the computer 154 closes valve 136 to preserve the vacuum in receptacle 132, manifold 128, tubes 124/126 and maintained by vacuum pump 140. Vent pipe 142 is then opened to atmosphere via valve 144. Valve 152 then opens the drainpipe 150 to the sewer system. Tank 138 can now drain into the sewer system. While tank 138 drains, people could continue to use the system 100 as vacuum is maintained in receptacle 132, which acts as a temporary holding means for people needing to urinate. Once tank 138 drains and the lower switch 148 is activated, then computer 154 closes the drain valve 152, closes vent valve 144, and opens valve 136 permitting communication between receptacle 132 and tank 138. The vacuum pump 140 then evacuates the tank 138 of air. Any urine contained in receptacle 132 while tank 138 was in the draining process, would then flow into tank 138. Alternatively a second vacuum pump could also be attached to tank 138 to ensure that there was sufficient vacuum in the tank before it was reconnected to the system via valve 136. Alternatively, sufficient sizing of manifold 128 could be undertaken to negate the need of receptacle 132.

System 100 could be periodically cleaned and sanitized by activating the system with the remote 122 and pouring diluted bleach or other sanitizing agent into the receptacle 102. Tank 138 could also be accessed via a port (not shown) to introduce sanitizing agents.

Figure 2:
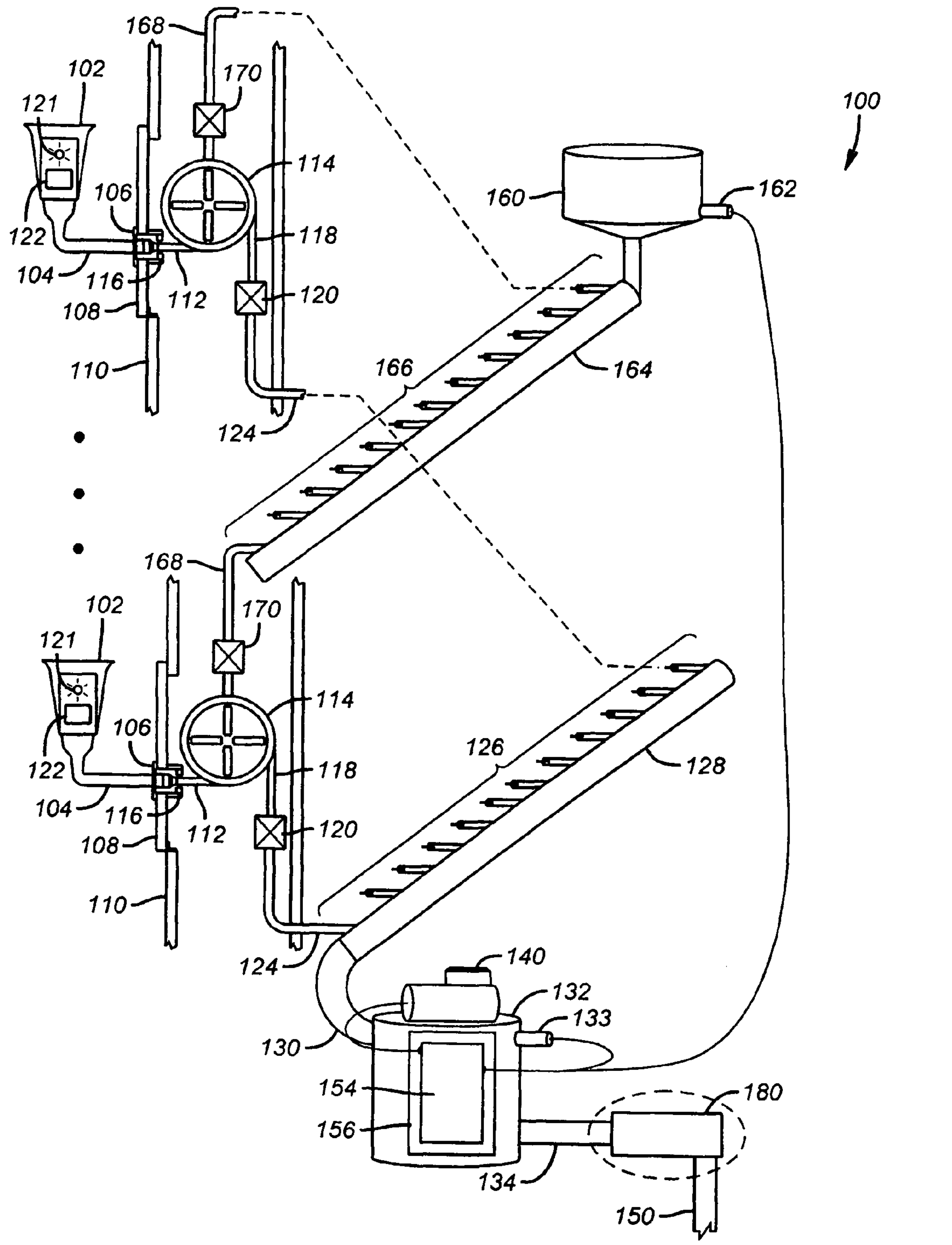
FIG. 2 is a schematic drawing showing a continuous discharge embodiment of the invention for use in multi-patent environments. Element 180 is depicted in detail in FIG. 3.
Figure 3:
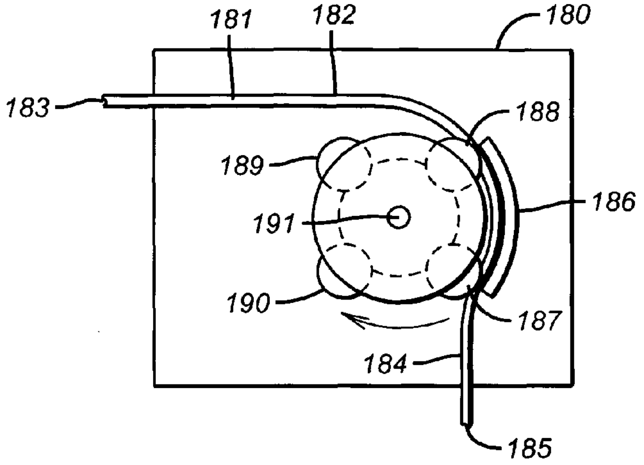
FIG. 3 is a schematic drawing showing operative elements of a peristaltic pump in the context of the invention.

An alternative embodiment is shown in FIGS. 2 and 3. Pump 180 is a peristaltic pump or other device capable of working in a vacuum environment to continuously pump urine from receptacle 132 through tubing 134 to the sewer via the sewer pipe 150. The peristaltic pump 180 includes a flexible tube 181 continuing tubing 134, having a proximal portion 182 with an inlet 183 and a distal portion 184 with an outlet 185, a platen 186 on one side of flexible tube 181, and at least two rollers 187 and 188 and as well 189, 190 disposed on a side of flexible tube 181 opposite from platen 186 for revolving about an axis 191 transverse to flexible tube 181. Each roller 187, 188 has sufficient diameter that a roller, e.g., 188 pressing the proximal portion 182 of tubing 181 against platen 186 seals the proximal portion 182 of tube 181 at the subatmospheric pressure of reservoir 132 when another roller, e.g. 187, releases sealing on the distal portion 184 of the flexible tubing 181, exposing outlet 185 to atmospheric pressure.

Figure 4:
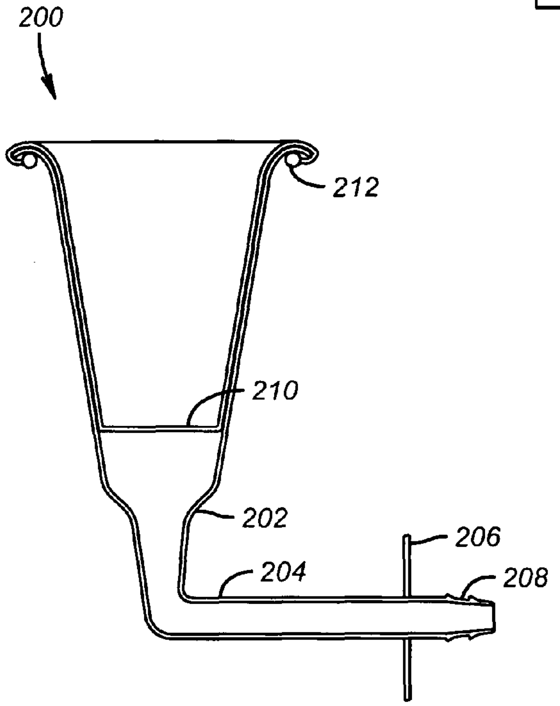
FIG. 4 is a schematic drawing showing a receptacle for use in accordance with the invention by a male urine donor.

FIG. 4 illustrates a disposable urine receptacle 200 designed for a male. The molded plastic portion 202 contains the receptacle which is molded to have a hydrophobic coating to repel (reduce the surface tension) of water. The design illustrates an exit at the bottom of the receptacle so that it can be used in a variety of positions. The tubular portion 204, is at a 90 degree angle to permit a more vertical installation on the wall. A wall cover plate 206, is shown for aesthetics and the barbed end is to permit the addition of tubing 112, illustrated in earlier figures.

This system 200 also includes a fabric or woven material 210 which has an elastic end 212 which is fitted over the top of the plastic receptacle 202. The purpose of this material is to eliminate splashing and also as a deodorant, by having a moisture activated deodorant/sanitizer formulated into material 210.

Figure 5:
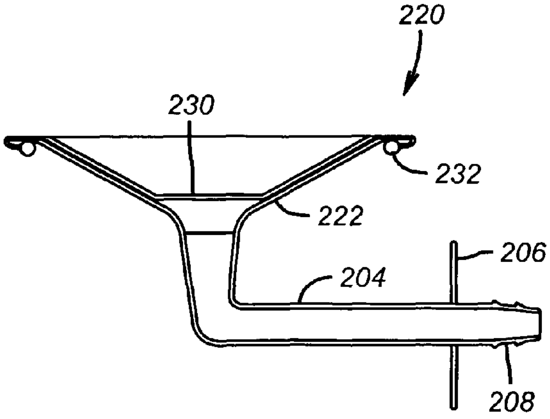
FIG. 5 is a schematic drawing showing a receptacle for use in accordance with the invention by a female urine donor.

FIG. 5 illustrates a receptacle 220 for a female. The materials for this receptacle are the same as for the male in FIG. 3. The receptacle base 222 is obround in shape with the long axis being illustrated in FIG. 4. The fabric or woven material 230 is shown attached using elastic 232 as before.

We claim:

1. A urine collecting and disposal system, comprising:

(a) a source for producing subatmospheric pressure;

(b) a reservoir maintained connected to said subatmospheric pressure source for supply of subatmospheric pressure, (c) a urine transport tube in valved fluid communication with said reservoir;

(d) a normally closed transport tube valve operatively arranged with respect to said transport tube and, for valving fluid communication of said reservoir with said transport tube to allow or disallow subatmospheric pressure from said reservoir in said transport tube distally from said valve;

(e) a urine receptacle in fluid communication with an end of said transport tube distal from said transport tube valve and said reservoir, said receptacle having access to atmospheric air, for receiving urine from a urine donor;

(f) a switch operatively associated with said transport tube valve and proximate said urine receptacle for switching said transport tube valve open and closed; and (g) a urine discharger spaced from said reservoir for removal and disposal of urine from said reservoir without exposing said reservoir to atmospheric pressure, said discharger including a receiving inlet in fluid communication with said reservoir for receiving urine from said reservoir at subatmospheric pressure, said inlet being sealingly closeable to maintain the reservoir at subatmospheric pressure during discharge of urine from said discharger, and a discharging outlet for discharging the urine at atmospheric pressure when said inlet is sealingly closed.

2. The system of claim 1 in which said discharger is continuous in operation.

3. The system of claim 2 in which said discharger comprises a peristaltic pump including a flexible tube having a proximal portion containing said inlet and a distal portion containing said outlet, a platen on one side of said flexible tube and at least two rollers disposed on a side of said flexible tube opposite from said platen for revolving about an axis transverse to said flexible tube, each roller having sufficient diameter that a roller pressing the proximal portion of said tubing against said platen seals said proximal portion of said tube at the subatmospheric pressure of said reservoir when another roller releases sealing on said distal portion of said flexible tubing, exposing said outlet to atmospheric pressure.

4. The system of claim 1 in which said discharger is discontinuous in operation.

5. The system of claim 4 further comprising a sanitation wash including:

(a) a source of a sanitizer;

(b) a valved conduit from said sanitizer source in fluid communication with said transport tube; and (c) a normally closed sanitizer conduit valve for opening and closing fluid communication from said sanitizer source into said transport tube.

6. The system of claim 5 in which the conduit is admitted into fluid communication with said transport tube between said receptacle and said transport tube valve.

7. The system of claim 1 wherein said transport tube is extendible from a normally retracted position for donation of urine into said receptacle when extended.

8. The system of claim 7 in which said transport tube is coilable and further comprising a tube carrier reel for retractably coiling said tube for storage in said retracted position.

9. The system of claim 1 comprising a plurality of urine receptacles each in valved fluid communication with a transport tube, each tube valved by a transport tube valve for such tube, each tube being unshared by another said receptacle, each transport tube communicating with a manifold interposed between said reservoir and the transport tube downstream from the tube valve of that transport tube.

10. The system of claim 1 in which the reservoir comprises a manifold.

11. A urine collecting and disposal system, comprising:

(a) a source for producing subatmospheric pressure;

(b) a reservoir to which is applied subatmospheric pressure from said subatmospheric pressure source, (c) a urine transport tube in valved fluid communication with said reservoir;

(d) a normally closed transport tube valve operatively arranged with respect to said transport tube, for valving fluid communication of said reservoir with said transport tube to allow or disallow subatmospheric pressure from said reservoir in said transport tube distally from said valve;

(e) a urine receptacle in fluid communication with an end of said transport tube distal from said transport tube valve and said reservoir, said receptacle having access to atmospheric air, for receiving urine from a urine donor;

(f) a switch operatively associated with said transport tube valve and proximate said urine receptacle for switching said transport tube valve open or closed; and (g) a urine discharger discontinuous in operation and spaced from said reservoir for removal and disposal of urine from said reservoir without exposing said reservoir to atmospheric pressure, said discharger including 1) a receiving inlet in fluid communication with said reservoir for receiving urine from said reservoir at subatmospheric pressure, said inlet being sealingly closeable to maintain the reservoir at subatmospheric pressure during discharge of urine from said discharger, 2) a discharging outlet for discharging the urine at atmospheric pressure when said inlet is sealingly closed, 3) an accumulator in normally open valved fluid communication with said reservoir for receiving urine from said reservoir and to which subatmospheric pressure is also applied from said subatmospheric pressure source, said accumulator having a normally closed discharge aperture at an inferior portion thereof for discharge of accumulated urine when said normally closed discharge aperture is opened and a normally closed superior aperture at a superior portion thereof for admission of atmospheric air when said normally closed superior aperture is opened;

4) a normally open reservoir valve between said reservoir and said accumulator for fluid and pressure communication between said reservoir and said accumulator when open and denial of pressure communication between said reservoir and said accumulator when closed;

5) a normally closed inferior accumulator valve operatively associated with said inferior aperture of said accumulator;

6) a normally closed superior accumulator valve operatively associated with said superior aperture of said accumulator;

7) an upper level switch operatively associated with said accumulator for signaling when urine is accumulated in said accumulator to a predetermined upper level;

8) a lower level switch operatively associated with said accumulator for signaling when urine is no higher than a predetermined lower level in said accumulator; and 9) a controller operatively associated with said level switches and said reservoir and accumulator valves, for closing said normally open reservoir valve and opening said normally closed accumulator valves on receipt of a signal from said upper level switch and for closing said accumulator valves and opening said reservoir valve upon receipt of a signal from said lower level switch.

12. A urine collecting and disposal system, comprising:

(a) a source for producing subatmospheric pressure;

(b) a reservoir to which is applied subatmospheric pressure from said subatmospheric pressure source, (c) a urine transport tube in valved fluid communication with said reservoir;

(d) a normally closed transport tube valve operatively arranged with respect to said transport tube, for valving fluid communication of said reservoir with said transport tube to allow or disallow subatmospheric pressure from said reservoir in said transport tube distally from said valve;

(e) a urine receptacle in fluid communication with an end of said transport tube distal from said transport tube valve and said reservoir, said receptacle having access to atmospheric air, for receiving urine from a urine donor, and having an upper opening remote from said end of said transport tube;

(f) a disposable sheath comprising a flexible fabric insertable into said receptacle, said sheath having an inferior opening and a superior elastic opening elastically securable over a boundary of said upper opening, for sheathing the interior of said receptacle and reducing splashing of urine donated into said receptacle (g) a switch operatively associated with said transport tube valve and proximate said urine receptacle for switching said transport tube valve open or closed; and (h) a urine discharger spaced from said reservoir for removal and disposal of urine from said reservoir without exposing said reservoir to atmospheric pressure, said discharger including 1) a receiving inlet in fluid communication with said reservoir for receiving urine from said reservoir at subatmospheric pressure, said inlet being sealingly closeable to maintain the reservoir at subatmospheric pressure during discharge of urine from said discharger, 2) a discharging outlet for discharging the urine at atmospheric pressure when said inlet is sealingly closed.

13. The system of claim 12 in which said sheath includes a water soluble deodorant deposited on said fabric and releasable when wetted by urine.

14. The system of claim 12 in which said sheath includes a water soluble sanitizing agent deposited on said fabric and releasable when wetted by urine.

* * * * *